(12) United States Patent
Fujii et al.

(10) Patent No.: US 8,038,443 B2
(45) Date of Patent: Oct. 18, 2011

(54) FIXTURE MOUNT FIXING TOOL

(75) Inventors: Naoto Fujii, Itabashi-ku (JP); Masashi Takahashi, Itabashi-ku (JP)

(73) Assignee: GC Corporation, Tokyo (JP)

( * ) Notice: Subject to any disclaimer, the term of this patent is extended or adjusted under 35 U.S.C. 154(b) by 191 days.

(21) Appl. No.: 12/495,106

(22) Filed: Jun. 30, 2009

(65) Prior Publication Data
US 2009/0325124 A1    Dec. 31, 2009

(30) Foreign Application Priority Data
Jun. 30, 2008    (JP) .................................. 2008-171821

(51) Int. Cl.
*A61C 8/00* (2006.01)
(52) U.S. Cl. ...................................... 433/173; 206/63.5
(58) Field of Classification Search .................. 433/172, 433/173, 174, 141, 77; 206/63.5
See application file for complete search history.

(56) References Cited

U.S. PATENT DOCUMENTS
2001/0019816 A1    9/2001    Kumar
2008/0032263 A1    2/2008    Bondar

FOREIGN PATENT DOCUMENTS
JP    2006-75427    3/2006

*Primary Examiner* — Cris L Rodriguez
*Assistant Examiner* — Eric Rosen
(74) *Attorney, Agent, or Firm* — Oblon, Spivak, McClelland, Maier & Neustadt, L.L.P.

(57) ABSTRACT

To provide a fixture mount fixing tool for preventing damage of a fixture in the storage container, when a fixture mount and the fixture are engaged, the fixture mount fixing tool includes a top part (2) having a bolt insertion through-hole (1) and a droop part (3) drooped therefrom, the bolt insertion through-hole (1) includes an engagement hole (4) engaged with a regular polygonal-shaped part (Zb) formed on an end part outer face of the fixture mount (Z), and/or the droop part (3) includes engagement faces contacted with plane parts on an outer face of the fixture mount (Z), and the droop part (3) includes a locking part (3b) locked with a container holding hole of a base table for holding the storage container (Y) or a locking part (3b) locked with engagement part formed on the side face of the container (Y).

6 Claims, 17 Drawing Sheets

FIXTURE MOUNT FIXING TOOL

BACKGROUND OF THE INVENTION

1. Field of the Invention

The present invention relates to a fixture mount fixing tool mounted on a fixture mount used in a dental implant treatment. This fixture mount fixing tool holds the fixture mount in an unrotatable state so as to make a self-tapping type implant fixture (it will be called a fixture below), which is engaged with the fixture mount, in an unrotatable state in a storage container, and prevents that the fixture is rotated to be damaged in the storage container when the fixture mount and the fixture are fastened with a bolt.

2. Description of the Conventional Art

A fixture used in a dental implant treatment is stored, while a sterilized state being kept, in a special storage container until being actually used.

The fixture stored in the special storage container is taken out from the storage container through an embedding instrument mounted to a hole at the oral cavity inner side of the fixture. Rotary drive force is transmitted to the embedding instrument for embedding the fixture in a jawbone at a lost tooth part. As for the embedding instrument, for example, Japanese Patent Application Laid-Open No. 2006-75427 describes an embedding instrument having a plurality of engagement projections at a top end part thereof. The plurality of the engagement projections are engaged with a plurality of recessed grooves formed on an inner face of a hole at the oral cavity side of the fixture, in which the hole is provided along a center axis of the fixture and has a female screw having a top end closed toward the inverse-oral cavity inner side. By engaging the plurality of the engagements projections formed at the top end part with the plurality of the recessed grooves formed on the inner face at the oral cavity side of the fixture, the rotary drive force can be transmitted to the fixture and also the fixture can be held.

The embedding instrument is engaged with the hole at the inner oral cavity side of the fixture by pushing and contacting the top end of the embedding instrument to the oral cavity inner side of the hole provided in the fixture, rotating the embedding instrument until positions of the recessed grooves of the fixture and the engagements projections of the embedding instrument are agreed, and thereafter inserting the engagement projections of the embedding instrument into the recessed grooves of the fixture. At this time, if the fixture contacted and pushed by the top end of the embedding instrument is rotated together with the embedding instrument, the embedding instrument cannot be engaged with the fixture. Thus, the fixture is made to be unrotatable in the storage container by forming projection parts on the bottom side in the storage container and contacting the projection parts with groove parts formed along cutting edge parts formed on a self-tapping screw at the top end side of the fixture.

By using the aforementioned storage container and the embedding instrument, the fixture can be simply handled through the embedding instrument without directly touching the fixture by hand. However, since the embedding instrument is only engaged with the fixture, there is a problem that the embedding instrument is easily separated. Therefore, a fixture mount has been used as a tool which certainly fixes the fixture. The fixture mount can not only engage a top end thereof with an end part at the oral cavity inner side of a fixture but also be fixed to the fixture with a bolt screwed through a through hole connecting with a female screw part formed at a bottom part of an engagement part of the fixture.

This fixture mount is engaged with the fixture by pushing and contacting the top end of the fixture mount to the oral cavity inner side of the hole provided in the fixture, rotating the fixture mount until the top end of the fixture mount becomes insertable into the hole provided in the fixture, and inserting the top end of the fixture mount into the hole. Thus, it is necessary to form projection parts on the bottom side in the storage container so as not to rotate the fixture, like the embedding instrument.

By using the storage container having the projection parts formed on the bottom side thereof and the fixture mount having the through hole, the fixture mount and the fixture are completely integrated with the bolt, and thus an implant treatment can be carried out in a state that the fixture is not fallen from the fixture mount.

However, when the fixture mount is fixed to the fixture with the bolt, the bolt is fastened by a driver or the like. Thus, when a torque larger than that required is added to the fixture, the fixture mount and the fixture are rotated integrally, and thus there is a problem that the top end part of the fixture is strongly contacted with the projection parts on the bottom side in the storage container so as to be damaged.

This problem does not occur if the bolt is fastened in a state that the fixture mount is held by hand. However, it is difficult to hold the fixture mount by hand because the size thereof is too small. Thus, since the bolt is fastened while the storage container is held, the fixture and the fixture mount are rotated integrally, and there is a problem that the top end part of the fixture is strongly contacted with the projection parts on the bottom side in the storage container so as to be damaged.

SUMMARY OF THE INVENTION

Problem to be Solved by the Invention

The present invention is made by taking the above points into consideration, and directed to provide a fixture mount fixing tool to be mounted on a fixture mount. This fixture mount fixing tool holds the fixture mount in an unrotatable state so as to make a fixture engaged with the fixture mount to be unrotatable in a storage container, and thereby prevents that the fixture is damaged by rotating in the storage container when the fixture mount and the fixture are fastened with a bolt.

Means for Solving the Problem

The present inventors carried out earnest works to solve the aforementioned problems and, as a result, they found out the followings to complete the present invention. A fixture mount fixing tool is mounted on a storage container, which stores a fixture, for holding a fixture mount in an unrotatable state. The fixture mount fixing tool includes a top part having a bolt insertion through-hole provided at a center thereof for inserting a bolt, and a droop part drooped from the top part toward the side face of the storage container. The bolt insertion through-hole of the top part includes an engagement hole to be engaged with a regular polygonal-shaped part which is formed on an end part outer face at the oral cavity inner side of the fixture mount, and/or the droop part is formed to have a shape having engagement faces in contact with plane parts which are formed on the side face of the fixture mount in parallel with a center axis. By taking this configuration, when the fixture mount fixing tool is mounted on the fixture mount engaged with the fixture, the fixture, the fixture mount, and the fixing mount fixing tool are integrated. Further, when a storage container holding hole is formed at a base table for holding a storage container, or a locking part locked with the engagement parts formed on the side face of the storage container are formed at the droop part, the fixture mount fixing tool is fixed to the base table or the storage container. As a result, the fixture mount and the fixture, which are integrated with the fixture mount fixing tool, are also in an unrotatable state. Thus, when the fixture mount and the fixture are fixed with the bolt while keeping this state, it can be prevented to cause a problem that the fixture is rotated in the storage container and a top end part of the fixture strongly contacts to projection parts on the bottom side in the storage container so as to be damaged when the bolt is fastened.

That is, the present invention is a fixture mount fixing tool to be mounted on a storage container for holding a fixture mount in an unrotatable state with respect to the storage container when the fixture mount is fixed to a self-tapping type implant fixture with a bolt screwed through a through-hole of the fixture mount. The self-tapping type implant fixture is unrotatably stored in the storage container by contacting projection parts formed on the bottom side in the storage container with groove parts formed along cutting edge parts formed at a top end of a self-tapping screw. A top end of the fixture mount, which has the through-hole connecting with a female screw part formed below recessed grooves of the fixture, is engaged with the recessed grooves formed on an inner face at the oral cavity inner side of the self-tapping type implant fixture. The fixture mount fixing tool includes a top part having a bolt insertion through-hole provided at a center thereof for inserting the bolt, and a droop part drooped from the top part toward the side face of the storage container. The bolt insertion through-hole of the top part includes an engagement hole to be engaged with a regular polygonal-shaped part formed on an end part outer face at the oral cavity inner side of the fixture mount, and/or the droop part includes engagement faces contacting with plane parts which are formed on the side face of the fixture mount in parallel with a center axis. Further, the droop part includes a locking part for being locked with a storage container holding hole formed in a base table for holding the storage container or for being locked with engagement parts formed on the side face of the storage container.

Further, in the configuration that the locking part is formed at the droop part, the locking part consists of is projection parts formed to downwardly project having approximately equal intervals at a lower end of the droop part, or the locking part consists of locking faces contacting with plane engagement parts which are formed on the side face of the storage container in parallel with a center axis. As a result, the fixture mount fixing tool can be easily locked with the storage container holding hole formed at the base table for holding the storage container or the engagement parts formed on the side face of the storage container, and thus it is preferable.

Effect of the Invention

The fixture mount fixing tool according to the present invention is mounted on a storage container for holding a fixture mount in an unrotatable state to the storage container when the fixture mount is fixed to a self-tapping type implant fixture with a bolt screwed through a through-hole of the fixture mount. The self-tapping type implant fixture is unrotatably stored in a storage container by contacting projection parts formed on the bottom side in a storage container with groove parts formed along cutting edge parts formed at a top end of a self-tapping screw. A top end of the fixture mount, which has the through-hole connecting with a female screw part formed below recessed grooves of the fixture is engaged with the recessed grooves formed on an inner face at the oral cavity inner side of the self-tapping type implant fixture. The fixture mount fixing tool includes a top part having a bolt insertion through-hole provided at a center thereof for inserting the bolt, and a droop part drooped from the top part toward the side face of the storage container. The bolt insertion through-hole of the top part includes an engagement hole to be engaged with a regular polygonal-shaped part formed on an end part outer face at the oral cavity inner side of the fixture mount, and/or the droop part includes engagement faces contacting with plane parts which are formed on the side face of the fixture mount in parallel with a center axis. Accordingly, when the fixture mount fixing tool is mounted on the fixture mount engaged with the fixture, the fixture, the fixture mount, and the fixing mount fixing tool are integrated. Further, the droop part includes a locking part for being locked with a storage container holding hole formed in a base table for holding the storage container or for being locked with an engagement parts formed on the side face of the storage container. Thus, when the fixture mount fixing tool is fixed to the base table or the storage container, the fixture mount and the fixture, which are integrated with the fixture mount fixing tool, become also in an unrotatable state. Therefore, when the fixture mount and the fixture are fixed with the bolt while keeping this state, it can be prevented to cause a problem that the fixture is rotated in the storage container and damaged by strong contact of a top end part of the fixture with projection parts on the bottom side in the storage container when the bolt is fastened.

Further, in the configuration that the droop part includes the locking part, the locking part consists of projection parts formed to downwardly project having approximately equal intervals at a lower end of the droop part, or the locking part consists of locking faces contacting with plane engagement parts which are formed on the side face of the storage container in parallel with a center axis. As a result, the fixture mount fixing tool can be easily locked with the storage container holding hole formed at the base table for holding the storage container or the engagement parts formed on the side face of the storage container.

DETAILED DESCRIPTION OF PREFERRED EMBODIMENT

A fixture mount fixing tool according to the present invention will be described in detail below with reference to the drawings.

Figure 1:
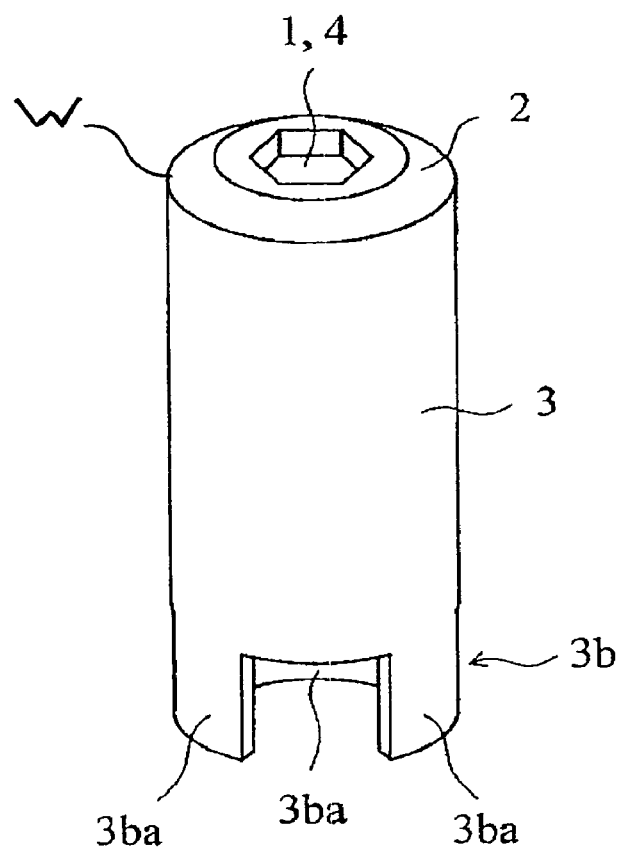
FIG. 1 is a perspective view for illustrating one example of a fixture mount fixing tool according to the present invention.
Figure 2:
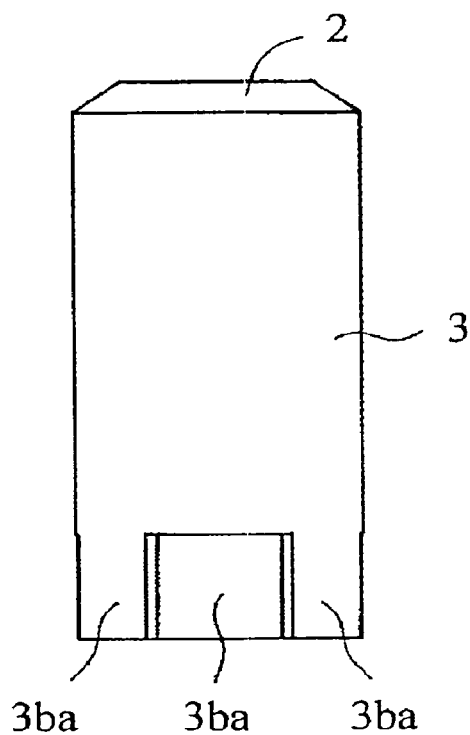
FIG. 2 is a front view in FIG. 1.
Figure 3:
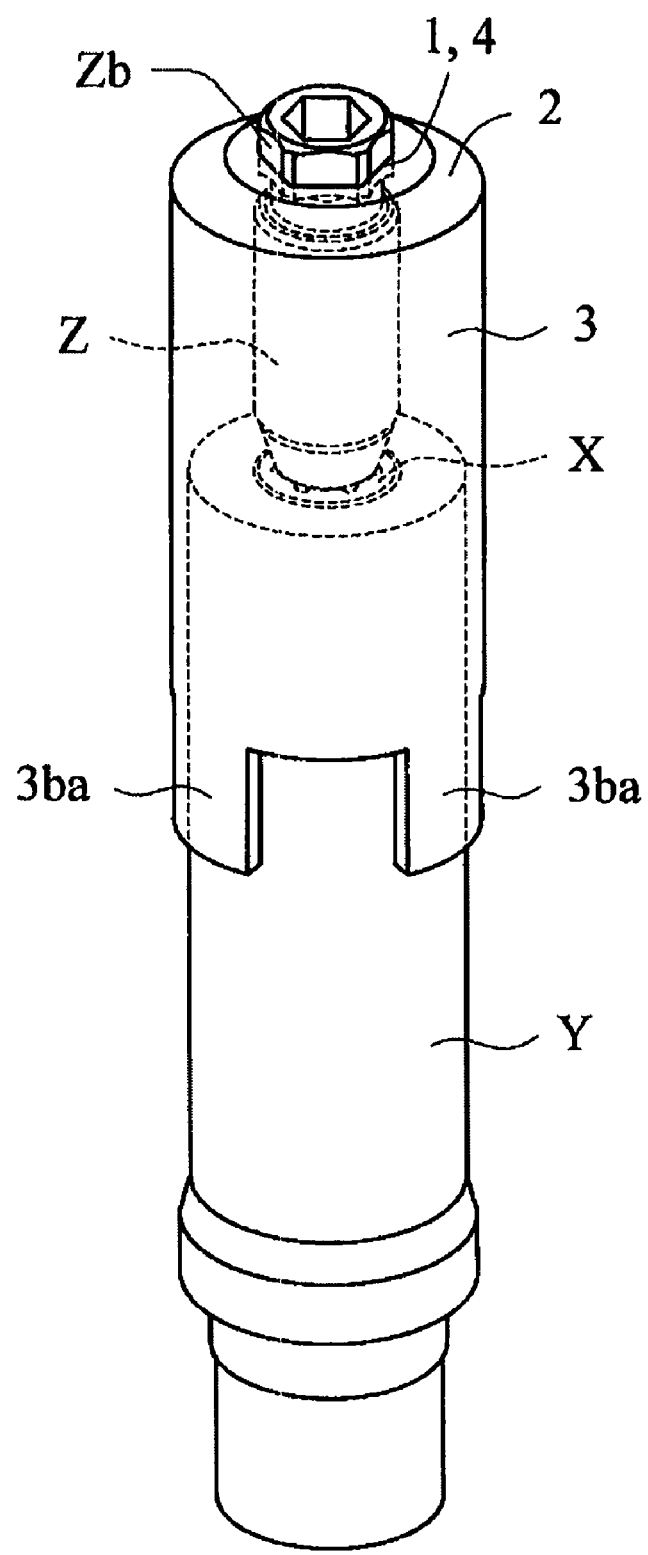
FIG. 3 is a perspective view for illustrating a state that the fixture mount fixing tool in FIG. 1 is mounted on a fixture mount engaged with a fixture in a storage container.
Figure 4:
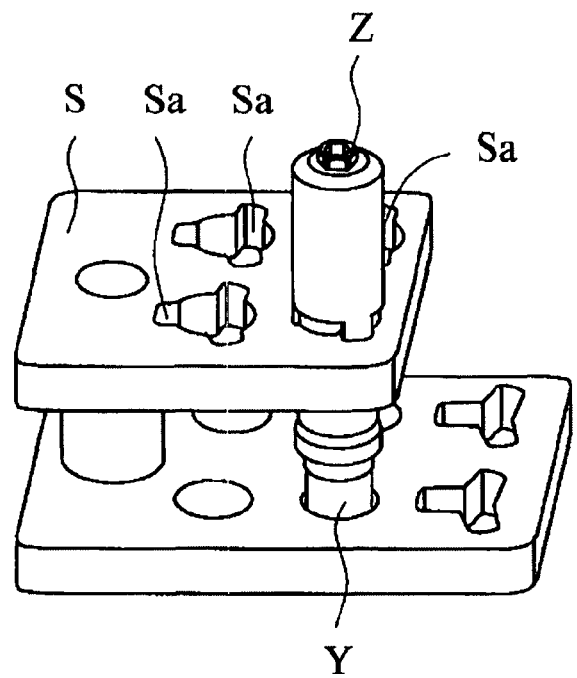
FIG. 4 is a perspective view for illustrating a state that the storage container in FIG. 3 is held at a base table, and a locking part formed at a droop part of a fixture mount fixing tool is locked with a storage container holding hole of the base table.
Figure 5:
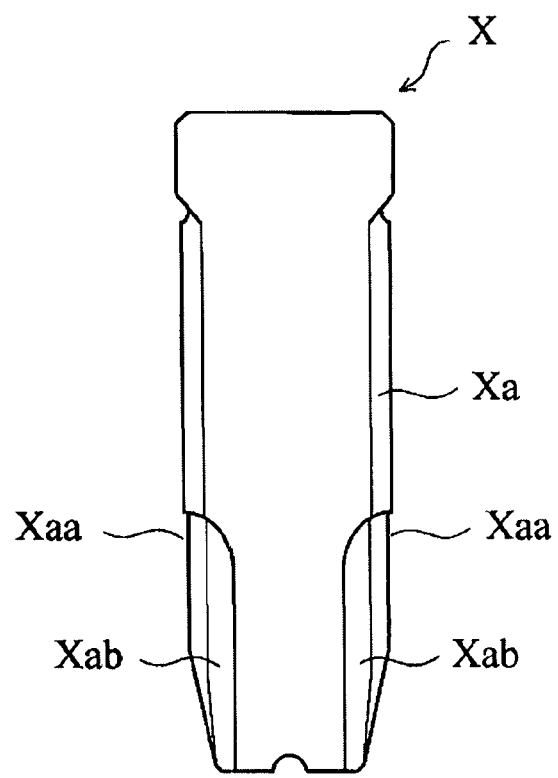
FIG. 5 is a front view for illustrating one example of a self-tapping type implant fixture.
Figure 6:
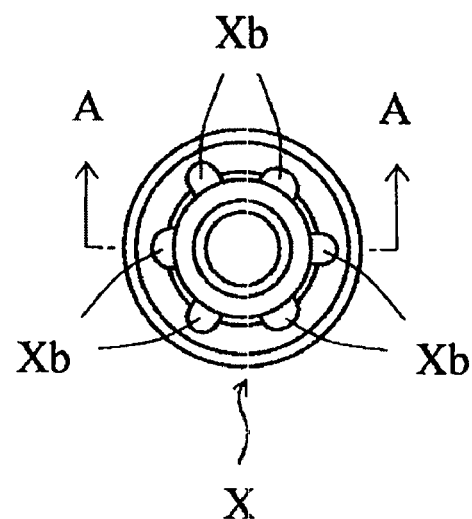
FIG. 6 is a plan view of FIG. 5.
Figure 7:
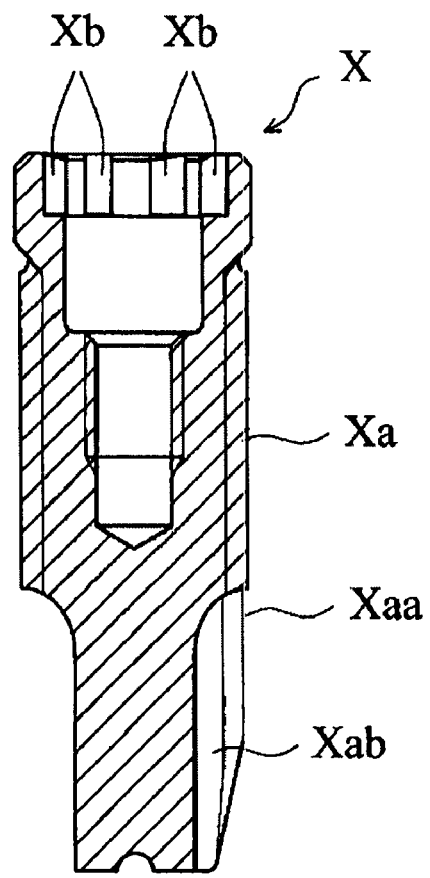
FIG. 7 is a sectional view taken at a line A-A in FIG. 6.
Figure 8:
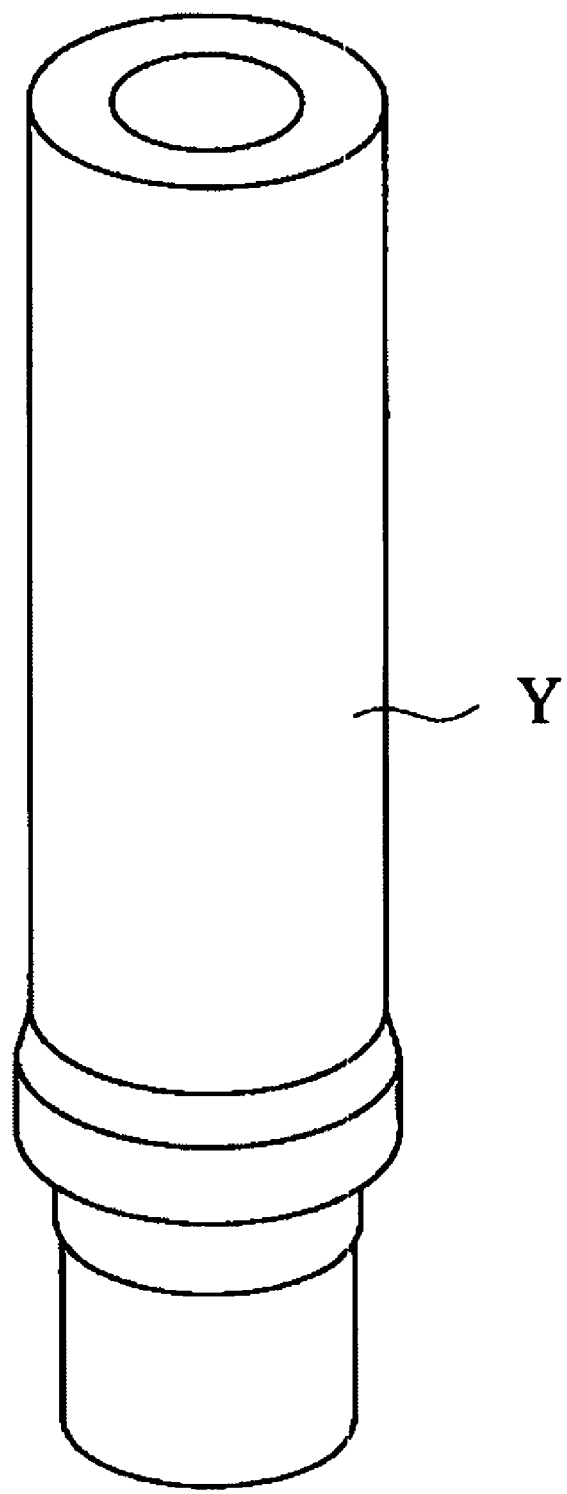
FIG. 8 is a perspective view for illustrating the storage container in FIG. 3.
Figure 9:
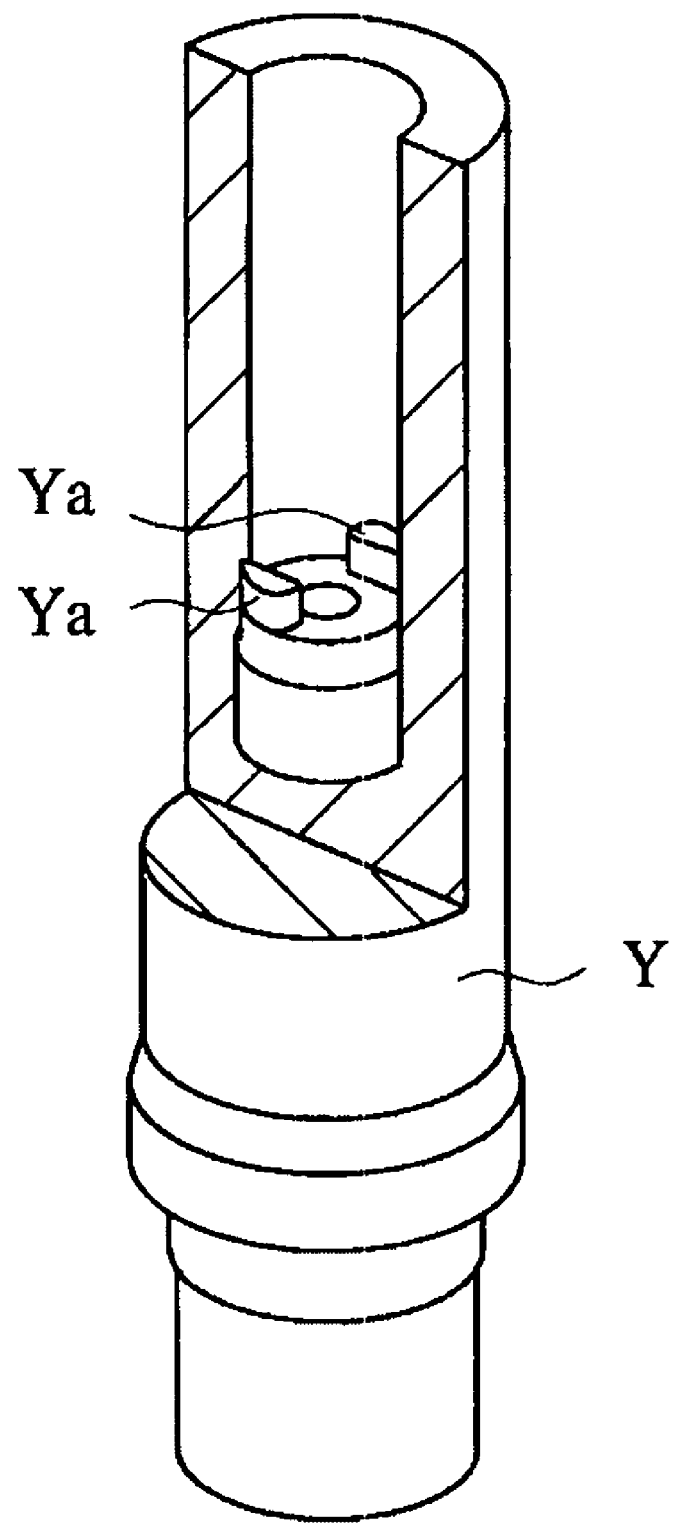
FIG. 9 is a partial sectional perspective view of the storage container in FIG. 8.
Figure 10:
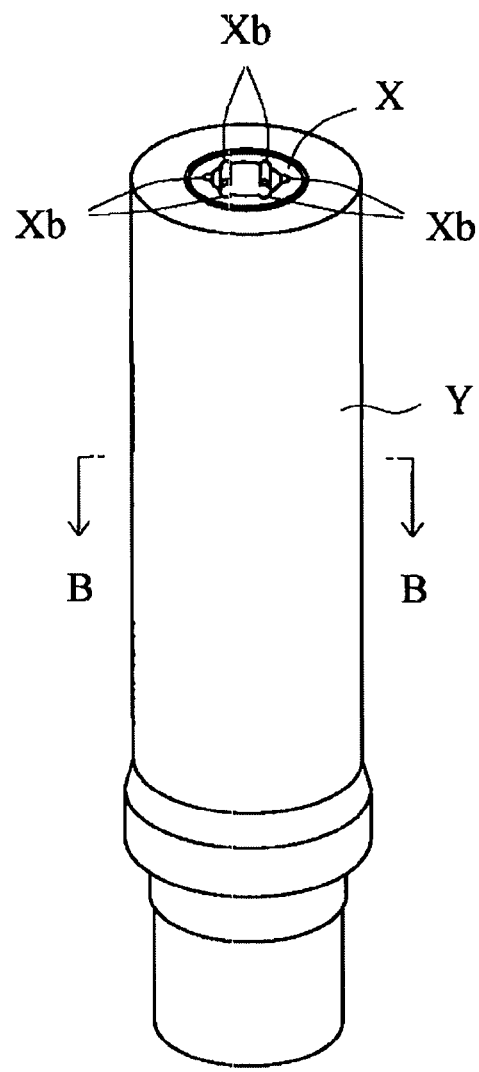
FIG. 10 is a perspective view for illustrating a state that the fixture in FIG. 5 is stored in the storage container of FIG. 8.
Figure 11:
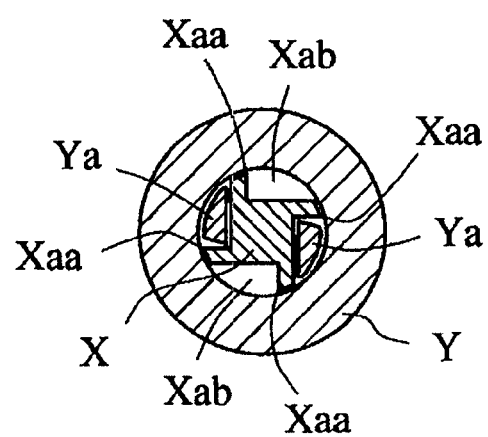
FIG. 11 is a sectional view taken at a line B-B in FIG. 10.
Figure 12:
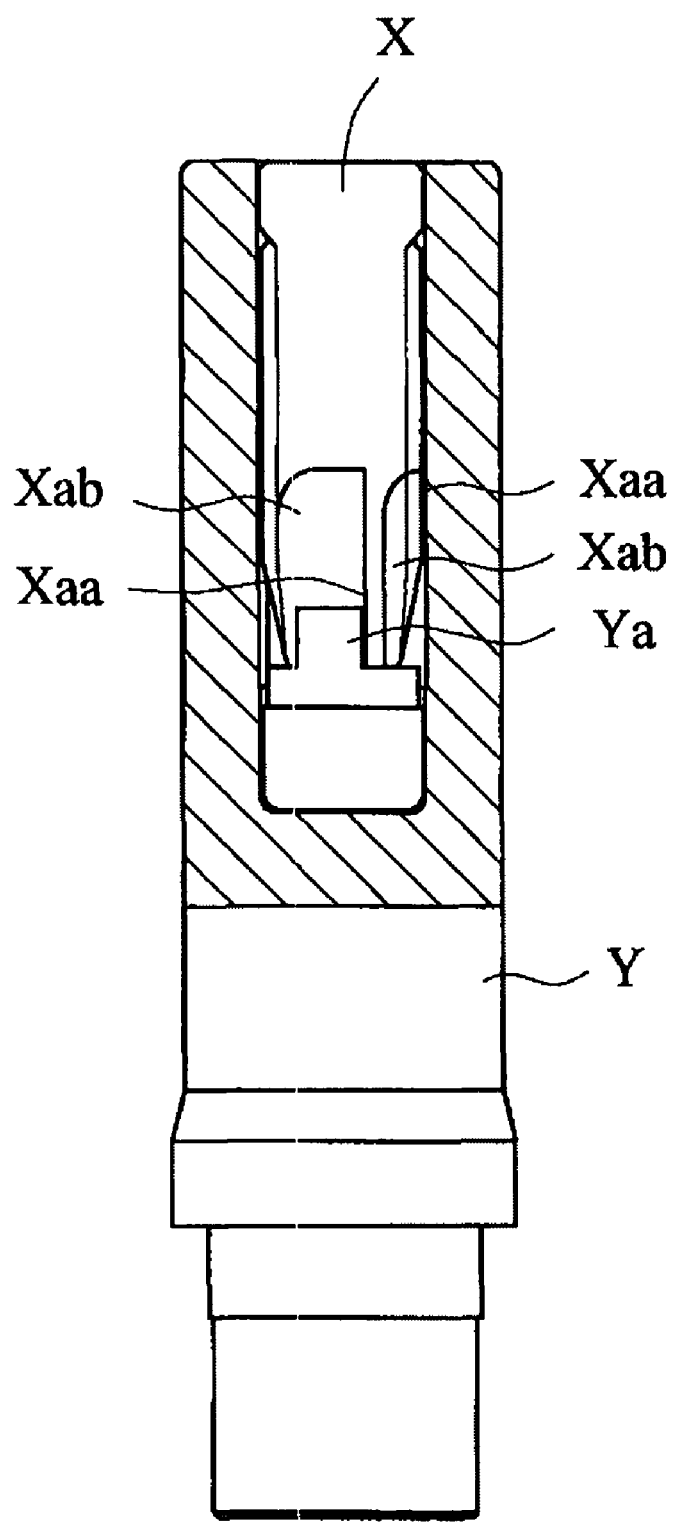
FIG. 12 is a partial sectional front view of a storage container in FIG. 10.
Figure 13:
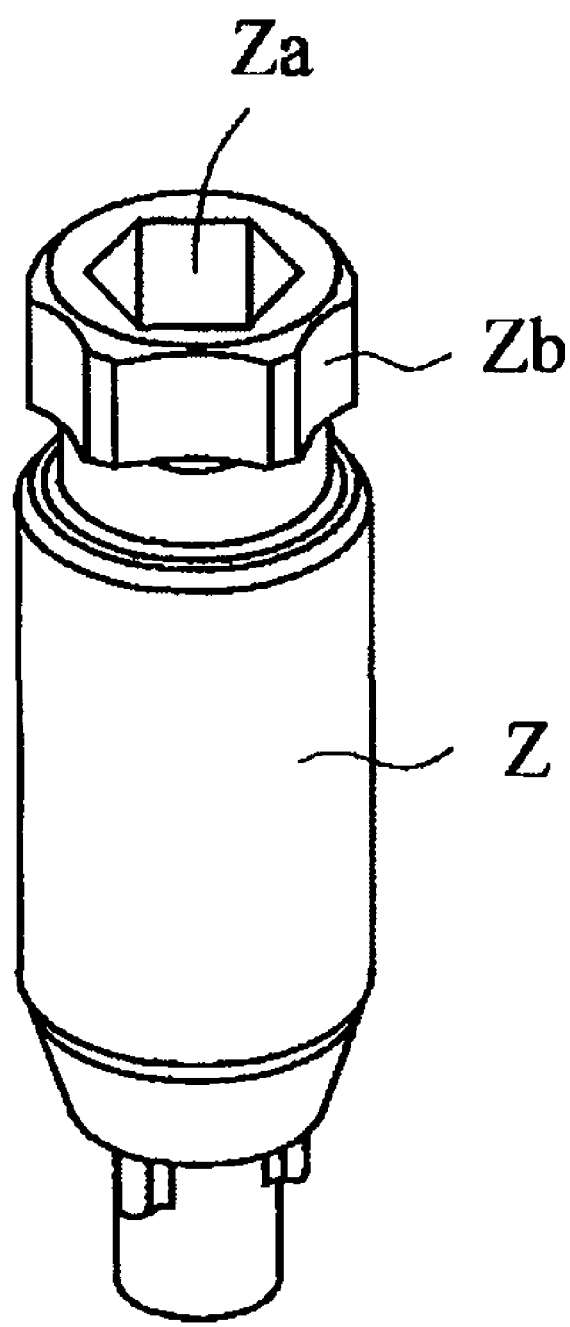
FIG. 13 is a perspective view for illustrating one example of the fixture mount in FIG. 3.
Figure 14:
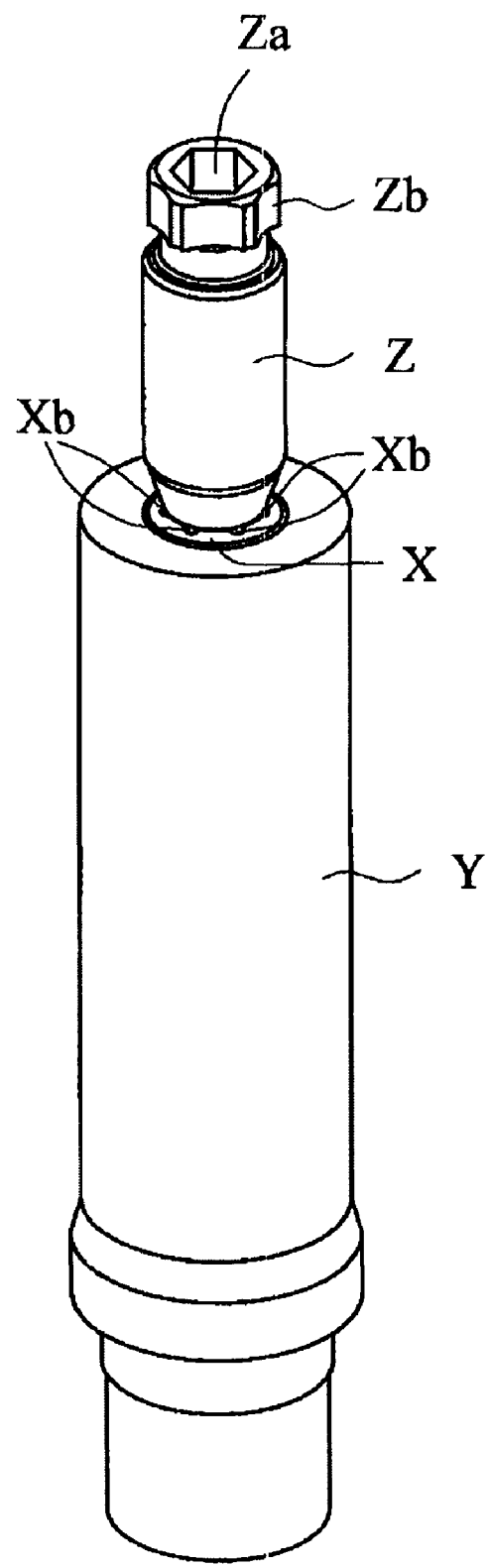
FIG. 14 is a perspective view for illustrating a state that the fixture mount in FIG. 13 is engaged with a fixture stored in the storage container in FIG. 10.
Figure 15:
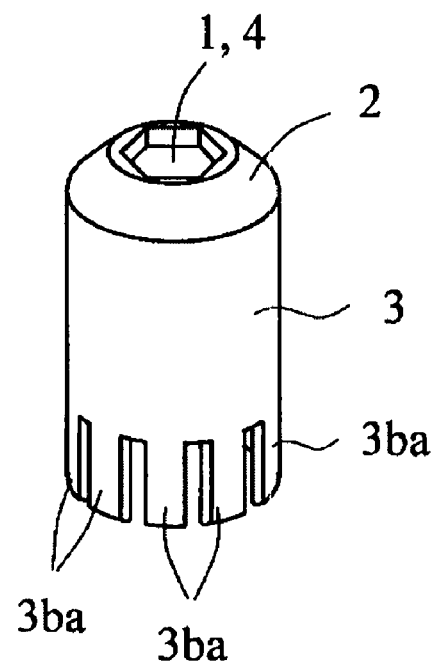
FIG. 15 is a perspective view for illustrating another example of a fixture mount fixing tool according to the present invention.
Figure 16:
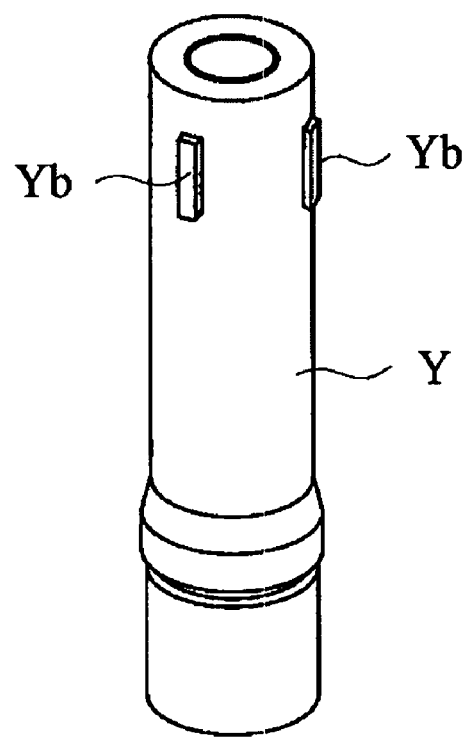
FIG. 16 is a perspective view for illustrating a storage container with which the fixture mount fixing tool in FIG. 15 is locked.
Figure 17:
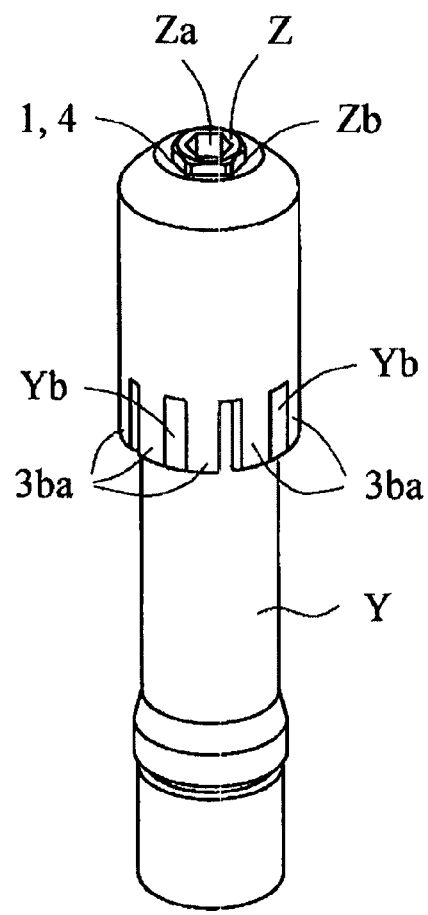
FIG. 17 is a perspective view for illustrating a state that the fixture mount fixing tool in FIG. 15 is mounted on the fixture mount in FIG. 13, and projection parts downwardly projecting to have approximately equal intervals at a lower end of a droop part of the fixture mount fixing tool are locked between projections formed on a side face of the storage container.
Figure 18:
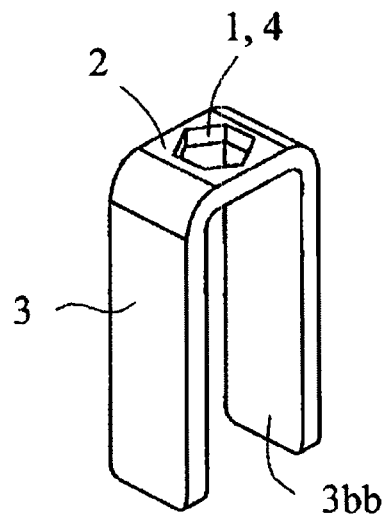
FIG. 18 is a perspective view for illustrating yet another example of a fixture mount fixing tool according to the present invention.
Figure 19:
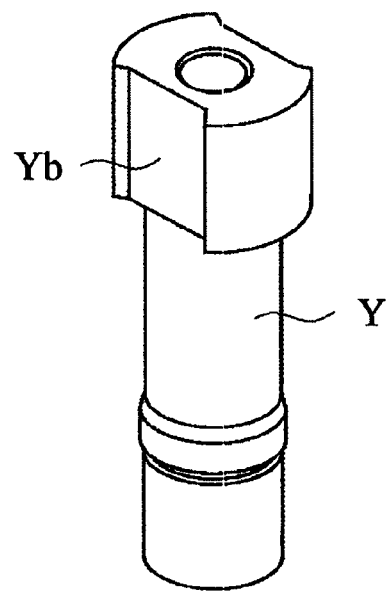
FIG. 19 is a perspective view for illustrating one example of a storage container with which the fixture mount fixing tool of FIG. 18 is locked.
Figure 20:
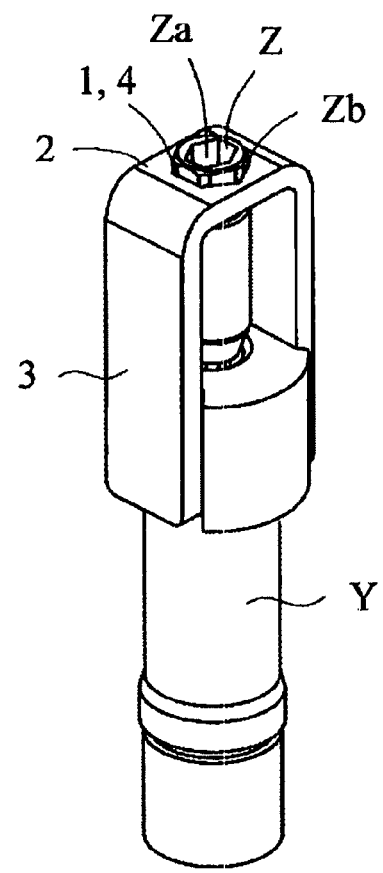
FIG. 20 is a perspective view for illustrating a state that the fixture mount fixing tool in FIG. 18 is mounted on the fixture mount in FIG. 13, and a locking face formed at a droop part of the fixture mount fixing tool is locked with a plane locking part which is formed on a side face of the storage container in parallel with a center axis.
Figure 21:
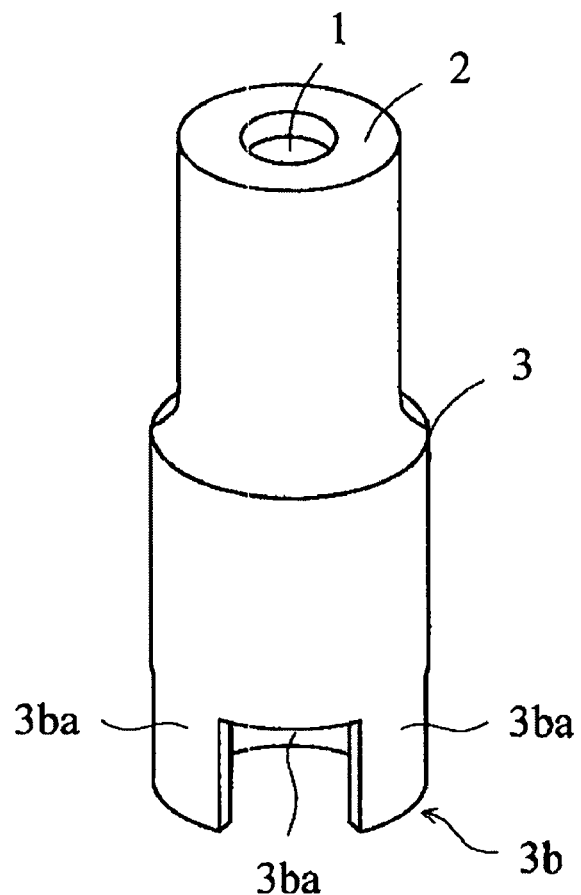
FIG. 21 is a perspective view for illustrating yet another example of a fixture mount fixing tool according to the present invention.
Figure 22:
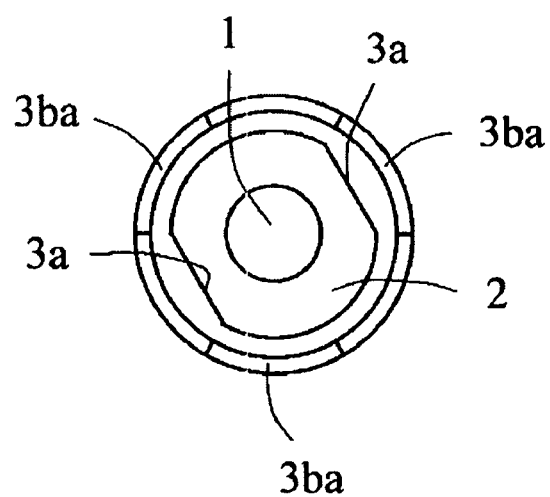
FIG. 22 is a bottom face view of the fixture mount fixing tool in FIG. 21.
Figure 23:
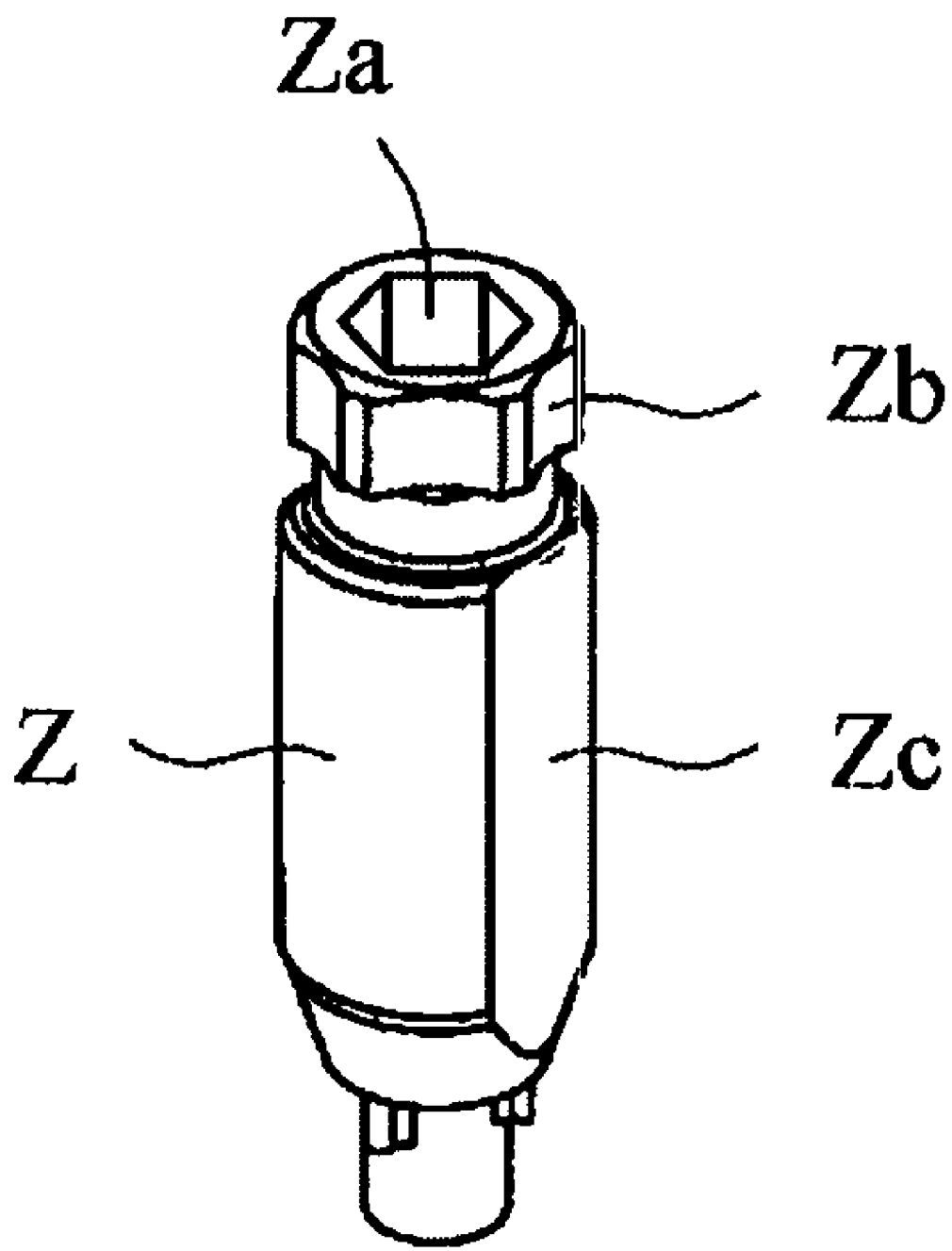
FIG. 23 is a perspective view for illustrating one example of a fixture mount mounted on the fixture mount fixing tool in FIG. 21.
Figure 24:
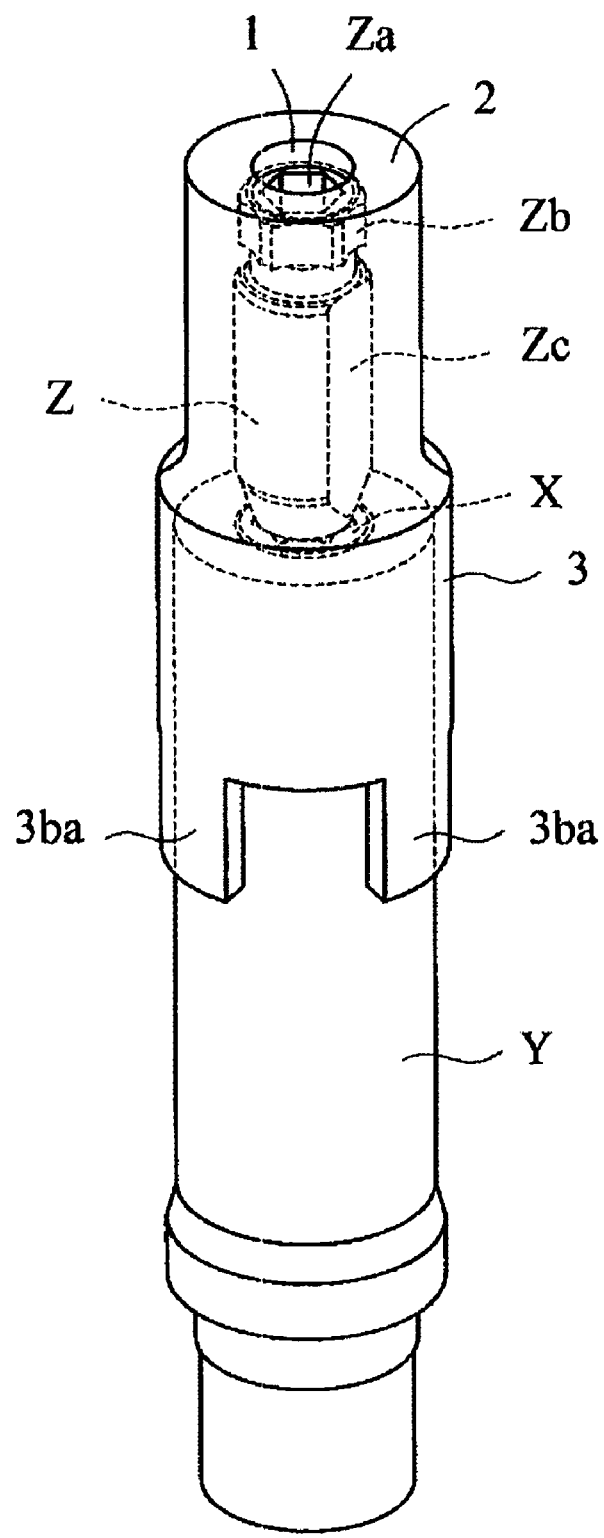
FIG. 24 is a perspective view for illustrating a state that the fixture mount fixing tool in FIG. 21 is mounted on the fixture mount in FIG. 21 engaged with the fixture stored in the storage container in FIG. 10.
Figure 25:
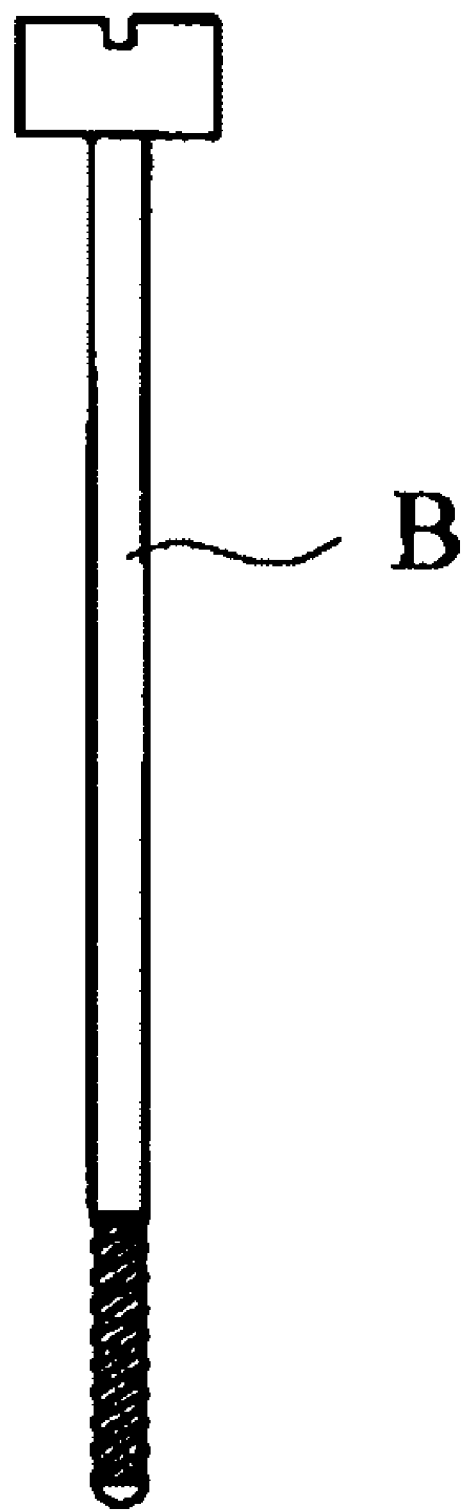
FIG. 25 is a front view for illustrating one example of a bolt used when fixing a fixture mount to a fixture.

FIG. 1 is a perspective view for illustrating one example of a fixture mount fixing tool W according to the present invention. FIG. 2 is a front view of FIG. 1. FIG. 3 is a perspective view for illustrating a state that the fixture mount fixing tool in FIG. 1 is mounted on a fixture mount engaged with a fixture in a storage container. FIG. 4 is a perspective view for illustrating a state that the storage container in FIG. 3 is held at a base table and a locking part formed at a droop part of a fixture mount fixing tool is locked with a storage container holding hole of the base table. FIG. 5 is a front view for illustrating one example of a self-tapping type implant fixture. FIG. 6 is a plan view in FIG. 5. FIG. 7 is a sectional view taken at a line A-A in FIG. 6. FIG. 8 is a perspective view for illustrating the storage container in FIG. 3. FIG. 9 is a partial sectional perspective view of the storage container in FIG. 8. FIG. 10 is a perspective view for illustrating a state that the fixture in FIG. 5 is stored in the storage container in FIG. 8. FIG. 11 is a sectional view taken at a line B-B in FIG. 10. FIG. 12 is a partial sectional front view of a storage container in FIG. 10. FIG. 13 is a perspective view for illustrating one example of the fixture mount in FIG. 3. FIG. 14 is a perspective view for illustrating a state that the fixture mount in FIG. 13 is engaged with a fixture stored in the storage container in FIG. 10. FIG. 15 is a perspective view for illustrating another example of a fixture mount fixing tool according to the present invention. FIG. 16 is a perspective view for illustrating a storage container with which the fixture mount fixing tool in FIG. 15 is locked. FIG. 17 is a perspective view to illustrate a state that the fixture mount fixing tool in FIG. 15 is mounted on the fixture mount in FIG. 13 and projection parts downwardly projecting to have approximately equal intervals at a lower end of a droop part of the fixture mount fixing tool are locked between projections formed on a side face of the storage container. FIG. 18 is a perspective view for illustrating yet another example of a fixture mount fixing tool according to the present invention. FIG. 19 is a perspective view for illustrating one example of a storage container with which the fixture mount fixing tool in FIG. 18 is locked. FIG. 20 is a perspective view for illustrating a state that the fixture mount fixing tool in FIG. 18 is mounted on the fixture mount in FIG. 13 and a locking face formed at a droop part of the fixture mount fixing tool is locked with a plane locking part which is formed on a side face of the storage container in parallel with a center axis. FIG. 21 is a perspective view for illustrating yet another example of a fixture mount fixing tool according to the present invention. FIG. 22 is a bottom face view of the fixture mount fixing tool in FIG. 21. FIG. 23 is a perspective view for illustrating one example of a fixture mount mounted on the fixture mount fixing tool in FIG. 21. FIG. 24 is a perspective view for illustrating a state that the fixture mount fixing tool in FIG. 21 is mounted on the fixture mount in FIG. 21 engaged with the fixture stored in the storage container in FIG. 10. FIG. 25 is a front view for illustrating one example of a bolt used when fixing a fixture mount to a fixture.

In these drawings, a self-tapping type implant fixture X includes groove parts Xab along cutting edge parts Xaa formed at a top end of a self-tapping type screw Xa. The self-tapping type implant fixture X has recessed grooves Xb on an inner face at the oral cavity inner side thereof. For example, the fixture X can have a configuration illustrated in FIGS. 5 to 7. As illustrated in FIG. 6, the fixture X includes six recessed grooves Xb on an inner face at the oral cavity inner side thereof. These recessed grooves Xb are used to engage an abutment or a jig for embedding a fixture. For example, when a fixture mount Z illustrated in FIG. 13 is mounted, three of the six recessed grooves Xb are engaged so as to mount the fixture mount Z.

As for a storage container Y in which the fixture X is stored, for example, a storage container Y illustrated in FIG. 8 can be used. As illustrated in a partial sectional view of FIG. 9, the storage container Y includes projection parts Ya on the bottom side in the storage container Y. As illustrated in FIGS. 10 to 12, when the fixture X is stored in the storage container Y, the groove parts Xab at the top end of the self-tapping screw Xa of the fixture X is made in contact with the projection parts Ya formed on the bottom side in the storage container Y so as to store the fixture X in an unrotatable state.

A fixture mount Z includes a through hole Za connecting to a female screw part formed at a bottom part of the recessed grooves Xb of the fixture X. A top end of the fixture mount Z is engaged with the recessed grooves Xb of the fixture X. The fixture mount Z can have a configuration illustrated in FIG. 13. In this configuration, three linear projection parts are formed at equal intervals on the top end side. In order to engage the fixture mount Z and the fixture X, a top end of the fixture mount Z is pushed and contacted with the oral cavity inner side of a hole bored in the fixture X stored in the storage container Y, the fixture mount Z is rotated until the three linear projection parts on the top end side of the fixture mount Z becomes insertable into three of the six recessed grooves Xb of the fixture X, and then these linear projection parts are inserted. In such a way, the fixture mount Z and the fixture X are engaged as illustrated in FIG. 14. At this time, if the fixture X, with which the fixture mount Z is pushed and contacted, is rotated in the storage container Y, the fixture mount Z cannot be engaged. Thus, the projection parts Ya are formed on the bottom side in the storage container Y in order to make them in contact with the groove parts Xab of the fixture X.

A bolt B as illustrated in FIG. 25 is screwed through the through hole Za of the fixture mount Z when fixing the fixture mount Z to the fixture X, and a base table S is for holding the storage container Y.

Then, a structure of a fixture mount fixing tool according to the present invention will be described.

A bolt insertion through-hole 1 is for inserting a bolt B and is provided at a center of a top part 2. The fixture mount fixing tool according to the present invention is used when fixing the fixture X and the fixture mount Z with the bolt B. Thus, the bolt insertion through-hole 1 is formed at the top part 2 in order to insert the bolt B and a tool such as a driver.

A droop part 3 is drooped from the top part 2 toward the side face of the storage container Y. The fixture mount fixing tool according to the present invention consists of the droop part 3 and the top part 2 at which the bolt insertion through-hole 2 is provided.

An engagement hole 4 is for engaging the fixture mount fixing tool with a regular polygonal-shaped part Zb formed on an end part outer face at the oral cavity inner side of the fixture mount Z. As for the fixture mount fixing tool according to the present invention, the bolt insertion through-hole 1 includes the engagement hole 4 to be engaged with the regular polygonal-shaped part Zb formed on the end part outer face at the oral cavity inner side of the fixture mount Z, and/or the droop part 3 is formed to have engagement faces 3a to be in contact with plane parts Zc formed on the side face of the fixture mount Z in parallel with a center axis. By mounting the fixture mount fixing tool according to the present invention on the fixture mount Z engaged with the fixture X, the fixture mount fixing tool according to the present invention can be integrated with the fixture X and the fixture mount Z.

An example of the fixture mount fixing tool according to the present invention can have a shape illustrated in FIGS. 1 and 2. In this fixture mount fixing tool, the bolt insertion through-hole 1 provided at the center of the top part 2 acts as the engagement hole 4 for engaging with the regular polygonal-shaped part Zb (a regular hexagonal shape in FIG. 3) formed on the end part outer face at the oral cavity inner side of the fixture mount Z.

In order to actually use the fixing mount fixing tool, firstly, while keeping a state that the linear projection parts on the top end side of the fixture mount Z are engaged with the recessed grooves Xb formed on the inner face at the oral cavity inner side of the fixture X in the storage container Y as illustrated in FIG. 14, the engagement hole 4 of the fixture mount fixing tool is engaged with the regular polygonal-shaped part Zb (a regular hexagonal shape in FIG. 14) formed on the end part outer face at the oral cavity inner side of the fixture mount Z so as to make a state illustrated in FIG. 3. In this state in FIG. 3, the fixture mount Z is engaged with the fixture X in the storage container Y, and the fixture mount fixing tool according to the present invention is engaged with the fixture mount Z. Therefore, the fixture mount fixing tool is integrated with the fixture X and the fixture mount Z.

Then, the three projection parts 3ba downwardly projecting from the fixture mount fixing tool are respectively locked with the three groove parts formed at a storage container holding hole Sa formed in the base table S as illustrated in FIG. 4 while keeping the state illustrated in FIG. 3. Thereby, the fixture mount fixing tool is fixed at the base table S so as to be unrotatable, and the fixture mount Z and the fixture X which are integrated with the fixture mount fixing tool also becomes unrotatable. While keeping this state, the bolt B as illustrated in FIG. 25 is screwed into a female screw formed in the fixture X through the through hole Za of the fixture mount Z so as to fix the fixture mount Z to the fixture X. In this state, since the fixture mount Z cannot be rotated, the groove parts Xab of the fixture X are not strongly contacted with the projection parts Ya on the bottom side in the storage container Y so that damaging of the fixture X can be prevented.

Another example of the fixture mount fixing tool according to the present invention is a fixture mount fixing tool illustrated in FIG. 15. Also in this fixture mount fixing tool, the engagement hole 4 of the fixture mount fixing tool is engaged with the regular polygonal-shaped part Zb (a regular hexagonal shape in FIG. 17) formed on the end part outer face at the oral cavity inner side of the fixture mount Z as illustrated in FIG. 17.

This fixture mount fixing tool has the projection parts 3ba downwardly projecting from the droop part 3 of approximately equal intervals. However, the projection parts 3ba are not locked with the base table S, but locked by fitting a linear projection engagement parts as illustrated in FIG. 16 Yb between the projection parts 3ba and 3ba. Since the fixture mount fixing tool is unrotatably locked with the storage container Y, the fixture mount Z and the fixture X which are integrated with the fixture mount fixing tool becomes unrotatable. Then, the storage container Y in a state illustrated in FIG. 17 is held by hand or the like, the bolt B is screwed into the female screw formed in the fixture X through the through hole Za of the fixture mount Z so as to fix the fixture mount Z to the fixture X.

Further, yet another example of the fixture mount fixing tool according to the present invention is a fixture mount fixing tool illustrated in FIG. 18. Also in this fixture mount fixing tool, the engagement hole 4 of the fixture mount fixing tool is engaged with the regular polygonal-shaped part Zb (a regular hexagonal shape in FIG. 20) formed on the end part outer face at the oral cavity inner side of the fixture mount Z as illustrated in FIG. 20.

This fixture mount fixing tool is also not locked with the base table S, but locked with the storage container Y. In the fixture mount fixing tool, as illustrated in FIG. 18, the engagement parts 3b provided at the droop part 3 are formed as the engagement faces 3bb to be in contact with the plane engagement parts Yb which are formed on the side face of the storage container Y in parallel with the center axis. That is, the storage container Y having the two opposed plane engagement parts Yb on the side face in parallel with the center axis is used as illustrated in FIG. 19. The fixture mount fixing tool includes two engagement faces 3bb and 3bb to be respectively in contact with the plane engagement parts Yb and Yb of the storage container Y. Further, after the fixture mount fixing tool is mounted so as to have a state as illustrated in FIG. 20, the storage container Y is held by hand or the like, and the bolt B is screwed into the female screw formed in the fixture X through the through hole Za of the fixture mount Z. Then, the fixture mount Z can be fixed at the fixture X.

Further, yet another example of the fixture mount fixing tool according to the present invention is a fixture mount fixing tool illustrated in FIG. 21. This fixture mount fixing tool is not engaged with the regular polygonal-shaped part Zb of the fixture mount Z but engaged by contacting the engagement faces 3a formed at an inner part of the fixture mount fixing tool as illustrated in FIG. 22 with plane parts Zc which are formed on the outer face of the fixture mount Z in parallel with the center axis as illustrated in FIG. 23. In this case, a hole of the top part 2 illustrated in FIGS. 21, 22 and 24 is the bolt insertion through-hole 1 for inserting the bolt B or for inserting a driver or the like used when screwing the bolt B.

This fixture mount fixing tool is engaged with the base table S. Three projection parts 3ba of the fixture mount fixing tool mounted to have a state as illustrated in FIG. 24 are respectively locked with three groove parts formed at the storage container holding hole Sa of the base table S, like the example of FIG. 4. Thereby, the fixture mount fixing tool is fixed at the base table S so as to be unrotatable, and the fixture mount Z and the fixture X which are integrated with the fixture mount fixing tool become to be unrotatable. While keeping this state, the bolt B as illustrated in FIG. 25 is screwed into the female screw formed in the fixture X through the engagement hole 4 of the fixture X and the through hole Za of the fixture mount Z so as to fix the fixture mount Z to the fixture X.

What is claimed is:

1. A dental fixture, comprising:
a fixture mount fixing tool;
a fixture mount;
a self-tapping type implant fixture; and
a storage container,
the fixture mount fixing tool being mounted on the storage container to hold the fixture mount in an unrotatable state with respect to the storage container, the fixture mount being fixed to the self-tapping type implant fixture, and the fixture mount remaining in the unrotatable state when a bolt is screwed through a through-hole of the fixture mount,
the self-tapping type implant fixture being unrotatably stored in the storage container by contacting projection parts formed on a bottom side of the storage container with groove parts of the self-tapping type implant fixture,
a top end of the fixture mount having the through-hole connecting with a female screw part of the self-tapping type implant fixture, the female screw part formed below recessed grooves of the self-tapping type implant fixture, the fixture mount being engaged with the recessed grooves formed on an inner face of the self-tapping type implant fixture, and
the fixture mount fixing tool including
a top part having a bolt insertion through-hole provided at a center thereof, and
a droop part drooped from the top part toward a side face of the storage container,
the bolt insertion through-hole of the top part including an engagement hole engaged with a regular polygonal-shaped part formed on an end part outer face of the fixture mount, or the droop part including engagement faces in contact with plane parts being formed on a side face of the fixture mount in parallel with a center axis, and
the droop part including a locking part to lock with a storage container holding hole formed in a base table to hold the storage container, or to lock with engagement parts formed on the side face of the storage container.

2. The dental fixture as claimed in claim 1,
wherein the locking part includes projection parts formed to downwardly project having approximately equal intervals at a lower end of the droop part.

3. The dental fixture as claimed in claim 1,
wherein the locking part includes locking faces in contact with the engagement parts formed on the side face of the storage container in parallel with the center axis shaft.

4. The dental fixture as claimed in claim 1,
wherein the projection parts formed on the bottom side of the storage container include only two individual projection parts that are diametrically opposed to one another.

5. The dental fixture as claimed in claim 1,
wherein the groove parts are formed along cutting edge parts of the self-tapping type implant fixture.

6. A dental fixture, comprising:
a fixture mount fixing tool;
a fixture mount;
a self-tapping type implant fixture; and
a storage container,
the fixture mount fixing tool being mounted on the storage container to hold the fixture mount in an unrotatable state with respect to the storage container, the fixture mount being fixed to the self-tapping type implant fixture, and the fixture mount remaining in the unrotatable state when a bolt is screwed through a through-hole of the fixture mount,
the self-tapping type implant fixture being unrotatably stored in the storage container by contacting projection parts formed on a bottom side of the storage container with groove parts of the self-tapping type implant fixture, and
the fixture mount fixing tool including
a top part having a bolt insertion through-hole provided at a center thereof, and
a droop part drooped from the top part toward a side face of the storage container,
the bolt insertion through-hole of the top part including an engagement hole engaged with a regular polygonal-shaped part formed on an end part outer face of the fixture mount, or the droop part including engagement faces in contact with plane parts being formed on a side face of the fixture mount in parallel with a center axis, and
the droop part including a locking part to lock with a storage container holding hole formed in a base table to hold the storage container, or to lock with engagement parts formed on the side face of the storage container.

* * * * *